United States Patent
Minami et al.

(10) Patent No.: US 10,302,542 B2
(45) Date of Patent: May 28, 2019

(54) PARTICULATE DETECTION SYSTEM

(71) Applicant: NGK SPARK PLUG CO., LTD., Nagoya-shi, Aichi (JP)

(72) Inventors: Hidekazu Minami, Kasugai (JP); Kaoru Hisada, Obu (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 195 days.

(21) Appl. No.: 15/598,376

(22) Filed: May 18, 2017

(65) Prior Publication Data
US 2017/0343463 A1 Nov. 30, 2017

(30) Foreign Application Priority Data

May 27, 2016 (JP) ................ 2016-106566

(51) Int. Cl.
| | |
|---|---|
| *G01N 15/00* | (2006.01) |
| *G01N 15/06* | (2006.01) |
| *F02D 41/20* | (2006.01) |
| *F02D 41/22* | (2006.01) |
| *G01N 27/70* | (2006.01) |
| *F01N 13/00* | (2010.01) |

(Continued)

(52) U.S. Cl.
CPC ....... *G01N 15/0656* (2013.01); *F01N 13/008* (2013.01); *F02D 41/1466* (2013.01); *F02D 41/20* (2013.01); *F02D 41/22* (2013.01); *F02D 41/222* (2013.01); *G01N 1/2252* (2013.01); *G01N 15/0606* (2013.01); *G01N 27/70* (2013.01); *F01N 2560/05* (2013.01); *F02D 2041/2003* (2013.01); *F02D 2041/2031* (2013.01); *G01N 2015/0046* (2013.01); *Y02T 10/40* (2013.01)

(58) Field of Classification Search
CPC ........ G01N 15/0656; G01N 2015/0046; F01N 2560/05
See application file for complete search history.

(56) References Cited

U.S. PATENT DOCUMENTS

| | | | |
|---|---|---|---|
| 8,652,240 B2 * | 2/2014 | Sugiyama | G01N 15/0656 60/275 |
| 2012/0234172 A1 | 9/2012 | Sugiyama et al. | |

(Continued)

FOREIGN PATENT DOCUMENTS

JP 2012-220423 A 11/2012

OTHER PUBLICATIONS

Communication dated Oct. 19, 2017 from the European Patent Office in counterpart application No. 17172841.3.

*Primary Examiner* — Blake A Tankersley
(74) *Attorney, Agent, or Firm* — Sughrue Mion, PLLC (57) ABSTRACT

In a particulate detection system (10), a control board (911), a high voltage generation board (913) and an isolation transformer (720) are respectively disposed in a first space (921*d*) and a second space (921*e*) separated from each other by an inner case (923). When electromagnetic noise is generated in the high voltage generation board (913) and the isolation transformer (720); specifically, at the primary winding of the isolation transformer 720, at the time of switching the primary current supply, the electromagnetic noise is blocked by the inner case (923). This configuration reduces the influence of electromagnetic noise generated in the primary winding on the control board (911).

2 Claims, 6 Drawing Sheets

(51) Int. Cl.
*G01N 1/22* (2006.01)
*F02D 41/14* (2006.01)

(56) References Cited

U.S. PATENT DOCUMENTS

| | | |
|---|---|---|
| 2012/0262182 A1 | 10/2012 | Matsuoka et al. |
| 2012/0285219 A1 | 11/2012 | Matuoka et al. |
| 2012/0312074 A1* | 12/2012 | Allmendinger .... G01N 15/0656 |
| | | 73/23.31 |
| 2014/0326873 A1 | 11/2014 | Kokubo |
| 2014/0352405 A1 | 12/2014 | Motomura et al. |
| 2015/0020574 A1 | 1/2015 | Motomura et al. |
| 2015/0114087 A1* | 4/2015 | Sugiyama ........... G01M 15/102 |
| | | 73/28.01 |

\* cited by examiner

PARTICULATE DETECTION SYSTEM

BACKGROUND OF THE INVENTION

1. Field of the Invention

The present invention relates to a particulate detection system which measures the amount of particulates such as soot contained in a gas under measurement.

2. Description of the Related Art

Conventionally, a particulate detection system has been known which measures the amount of particulates (e.g., soot) contained in a gas under measurement (for example, exhaust gas discharged from an internal combustion engine or the like) (see, for example, Patent Document 1).

Such a particulate detection system includes, for example, a particulate sensor, a high voltage generation section, a primary current control section, and a sensor signal processing section (Patent Document 1).

The particulate sensor is exposed to the gas under measurement, and generates a sensor signal corresponding to the result of detection of particulates. The high voltage generation section includes a transformer having a primary winding and a secondary winding. The high voltage generation section supplies to the particulate sensor a high voltage generated from the secondary winding as a result of switching the supply of primary current to the primary winding. The primary current control section controls the primary current flowing through the primary winding. The sensor signal processing section processes the sensor signal generated by the particulate sensor.

The above-described particulate detection system includes an isolation transformer to suppress the influence, on the sensor signal processing section, of electromagnetic noise generated in the secondary winding. Notably, the isolation transformer is configured such that its primary-side and secondary-side cores are separated from each other with a small gap formed therebetween so as to isolate the primary-side and secondary-side cores from each other. Further, a common magnetic flux passes through the primary-side and secondary-side cores, whereby a transforming action is achieved.

The particulate detection system also includes an inner metal case and an outer metal case for shielding electromagnetic noise. The inner metal case surrounds the secondary winding, the secondary-side core, and the high voltage generation section. The outer metal case surrounds the inner metal case, the primary winding, the primary-side core, the primary current control section, and the sensor signal processing section.

The particulate detection system having such a configuration can suppress the influence, on the sensor signal processing section, of electromagnetic noise generated in the secondary winding. This is because the inner metal case can shield the electromagnetic noise generated in the secondary winding. As a result, it is possible to suppress a decrease in particulate detection accuracy due to the electromagnetic noise generated in the secondary winding.

[Patent Document 1] Japanese Patent Application Laid-Open (kokai) No. 2012-220423

3. Problems to be Solved by the Invention

In the above-described particulate detection system, a member for blocking electromagnetic noise is provided between the primary winding and the sensor signal processing section. Therefore, when electromagnetic noise is generated in the primary winding, the generated electromagnetic noise may influence the sensor signal processing section.

Notably, the primary winding generates a lower voltage as compared with the secondary winding, and the electromagnetic noise generated in the primary winding is of smaller magnitude than that generated in the secondary winding. Therefore, the influence of the electromagnetic noise generated in the primary winding on the sensor signal processing section is smaller than the influence of the electromagnetic noise generated in the secondary winding.

However, in the case where the sensor signal has a very small current value, the electromagnetic noise generated in the primary winding may affect the signal processing in the sensor signal processing section and lower the particulate detection accuracy.

SUMMARY OF THE INVENTION

It is therefore an object of the present invention to provide a particulate detection system which can suppress the influence, on detection of particulates, of electromagnetic noise generated in the primary winding of an isolation transformer used therein.

The above object has been achieved by providing, in a first aspect of the invention, (1) a particulate detection system comprising a particulate sensor, a high voltage generation section, a primary current control section, and a sensor signal processing section, and further comprising an inner shield and an outer shield.

The particulate sensor generates a sensor signal corresponding to a result of particulate detection. The high voltage generation section includes a transformer having a primary winding and a secondary winding and supplies to the particulate sensor a high voltage generated from the secondary winding as a result of switching a primary current supply to the primary winding. The primary current control section controls the primary current flowing through the primary winding. The sensor signal processing section processes the sensor signal generated by the particulate sensor.

The inner shield covers the high voltage generation section and is formed of a material which blocks electromagnetic noise. The outer shield covers the sensor signal processing section and the inner shield and is formed of a material which blocks electromagnetic noise.

In the particulate detection system (1) having such a configuration, the high voltage generation section and the sensor signal processing section are respectively disposed in different spaces which are separated from each other by the inner shield. In the case where the particulate detection system has such a configuration, even when electromagnetic noise is generated in the high voltage generation section; specifically, at the primary winding of the transformer, at the time of switching the primary current supply, the electromagnetic noise is blocked by the inner shield. As a result, it is possible to reduce the influence of the electromagnetic noise generated in the primary winding on the sensor signal processing section.

Also, since the outer shield is provided, it is possible to prevent external electromagnetic noise from reaching the sensor signal processing section. Therefore, it is possible to reduce the influence of external noise on the sensor signal processing section.

As a result, the particulate detection system can reduce the influence of electromagnetic noise generated in the primary winding on the sensor signal processing section. Thus, the particulate detection system can suppress a decrease in the particulate detection accuracy due to the influence of electromagnetic noise. Further, the particulate detection system can reduce the influence of external electromagnetic noise on the sensor signal processing section.

Notably, the primary current control section may be disposed in the shielded space in which the high voltage generation section is disposed or in the shielded space in which the sensor signal processing section is disposed.

In a preferred embodiment (2) of the above-described particulate detection system (1), the primary current control section is disposed inside the inner shield.

In the case where the particulate detection system has such a configuration, even when electromagnetic noise is generated in the primary current control section, the inner shield prevents the electromagnetic noise from reaching the sensor signal processing section. Therefore, it is possible to suppress the influence of electromagnetic noise generated in the primary current control section on the sensor signal processing section.

As a result, the particulate detection system having such a configuration can suppress a decrease in the particulate detection accuracy due to influence of electromagnetic noise generated in the primary current control section.

Effects of the Invention

According to the particulate detection system of the present invention, the influence of electromagnetic noise generated in the primary winding on the sensor signal processing section can be reduced. Therefore, it is possible to suppress a decrease in particulate detection accuracy due to influence of electromagnetic noise. Further, it is possible to reduce the influence of external electromagnetic noise on the sensor signal processing section.

BRIEF DESCRIPTION OF THE DRAWINGS

FIGS. 1A and 1B are explanatory views illustrating the overall configuration of a particulate detection system according to a first embodiment, wherein

DESCRIPTION OF REFERENCE NUMERALS

Reference numerals used to identify various features in the drawings include the following.

10 . . . particulate detection system; 100 . . . particulate sensor; 300 . . . sensor drive section; 440 . . . power supply section; 600 . . . sensor control section; 700 . . . electric circuit section; 710 . . . power supply circuit; 710a . . . first power supply circuit; 710b . . . second power supply circuit; 711a . . . first discharge voltage control circuit; 711b . . . second discharge voltage control circuit; 712a . . . first transformer drive circuit; 712b . . . second transformer drive circuit; 720 . . . isolation transformer; 720a . . . first isolation transformer; 720b . . . second isolation transformer; 730 . . . corona current detection system; 740 . . . ion current detection system; 751 . . . first rectification circuit; 752 . . . second rectification circuit; 900 . . . circuit housing; 911 . . . control board; 913 . . . high voltage generation board; 921 . . . outer case; 921a . . . outer body member; 921b . . . outer cover member; 921c . . . partition wall; 921d . . . first space; 921e . . . second space; 923 . . . inner case; 923a . . . inner body member; 923b . . . inner cover member; 924 . . . first insulating member; 925 . . . second insulating member; 926 . . . third insulating member.

DETAILED DESCRIPTION OF THE PREFERRED EMBODIMENTS

Embodiments to which the present invention is applied will next be described with reference to the drawings. However, the present invention should not be construed as being limited thereto.

[1. First Embodiment]
[1-1. Overall Configuration]

The configuration of a particulate detection system according to the present embodiment will next be described.

Figure 1A:
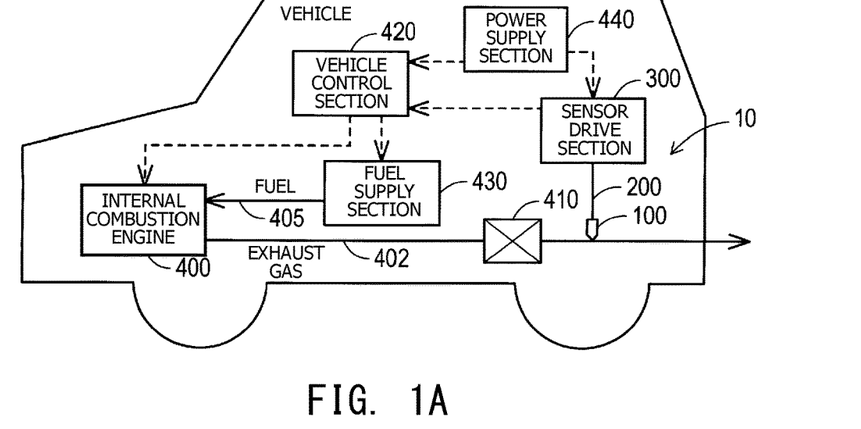
FIG. 1A is an explanatory view exemplifying a general configuration of a vehicle on which a particulate detection system is mounted.
Figure 1B:
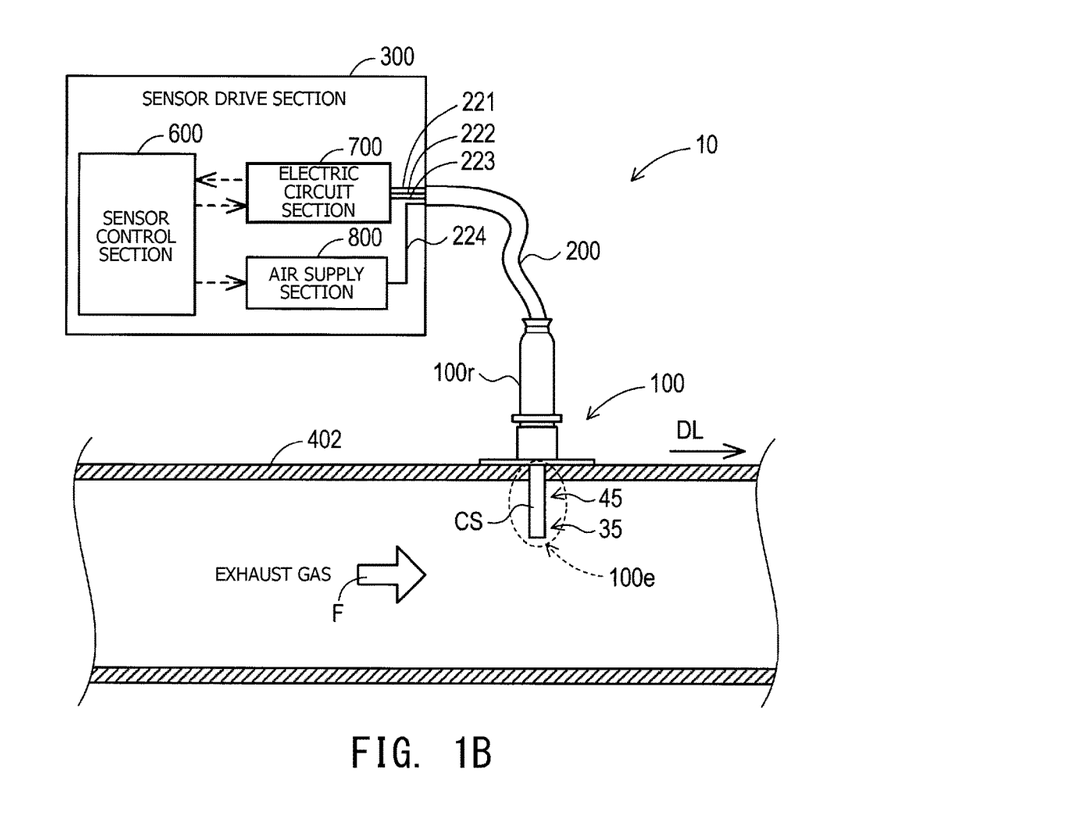
FIG. 1B is an explanatory view exemplifying a general configuration of the particulate detection system attached to the vehicle.

FIGS. 1A and 1B are explanatory views used for describing the overall configuration of a particulate detection system 10 according to the first embodiment. FIG. 1A is an explanatory view schematically exemplifying a general configuration of a vehicle 500 on which the particulate detection system 10 is mounted. FIG. 1B is an explanatory view exemplifying a general configuration of the particulate detection system 10 attached to the vehicle 500.

The particulate detection system 10 includes a particulate sensor 100, a cable 200, and a sensor drive section 300, and measures the amount of particulates such as soot contained in exhaust gas discharged from an internal combustion engine 400. The internal combustion engine 400, which is a power source of the vehicle 500, is a diesel engine or the like.

The particulate sensor 100 is attached to an exhaust pipe 402 extending from the internal combustion engine 400, and is electrically connected to the sensor drive section 300 through the cable 200. In the present embodiment, the particulate sensor 100 is attached to a portion of the exhaust pipe 402, which portion is located downstream of a filter apparatus 410 (for example, a DPF (diesel particulate filter)). The particulate sensor 100 outputs to the sensor drive section 300 a signal which correlates with the amount of particulates contained in the exhaust gas.

The sensor drive section 300 drives the particulate sensor 100 and detects (measures) the amount of particulates contained in the exhaust gas based on the signal input from the particulate sensor 100. The "amount of particulates contained in the exhaust gas" detected by the sensor drive section 300 may be a value which is proportional to the sum of the surface areas of particulates contained in the exhaust gas, or a value which is proportional to the sum of the masses of the particulates. Alternatively, the amount of particulates contained in the exhaust gas may be a value which is proportional to the number of particulates contained in a unit volume of the exhaust gas. The sensor drive section 300 is electrically connected to a vehicle control section 420 on the vehicle 500 side, and outputs to the vehicle control section 420 a signal representing the detected amount of particulates contained in the exhaust gas.

In response to the signal input from the sensor drive section 300, the vehicle control section 420 controls the combustion state of the internal combustion engine 400, the amount of fuel supplied from a fuel supply section 430 to the internal combustion engine 400 through a fuel pipe 405, etc. The vehicle control section 420 may be configured to warn a driver of the vehicle 500 of a deterioration or anomaly of the filter apparatus 410, for example, when the amount of particulates contained in the exhaust gas is greater than a predetermined amount. The sensor drive section 300 and the vehicle control section 420 are electrically connected to a power supply section 440, and electric power is supplied from the power supply section 440 to the sensor drive section 300 and the vehicle control section 420.

As shown in FIG. 1B, the particulate sensor 100 has a cylindrical distal end portion 100e, and is fixed to the outer surface of the exhaust pipe 402 such that the distal end portion 100e is inserted into the exhaust pipe 402. In the present embodiment, the distal end portion 100e of the particulate sensor 100 is inserted approximately perpendicular to an extension direction DL of the exhaust pipe 402. A casing CS of the distal end portion 100e has an inflow hole 45 and a discharge hole 35 formed on the surface of the casing CS. The inflow hole 45 introduces the exhaust gas into the interior of the casing CS, and the discharge hole 35 discharges the introduced exhaust gas to the outside of the casing CS. A portion of the exhaust gas flowing through the exhaust pipe 402 is introduced into the interior of the casing CS of the distal end portion 100e through the inflow hole 45. Particulates contained in the introduced exhaust gas are electrified by ions (positive ions in the present embodiment) generated by the particulate sensor 100. The exhaust gas containing the electrified particulates is discharged to the outside of the casing CS through the discharge hole 35. The internal structure of the casing CS and the specific structure of the particulate sensor 100 will be described below.

The cable 200 is attached to a rear end portion 100r of the particulate sensor 100. The cable 200 includes a first wiring line 221, a second wiring line 222, a signal line 223, and an air supply tube 224 bundled together. Each of the wiring lines 221 to 223 and the air supply tube 224, which constitute the cable 200, is formed of a flexible member. The first wiring line 221, the second wiring line 222, and the signal line 223 are electrically connected to an electric circuit section 700 of the sensor drive section 300, and the air supply tube 224 is connected to an air supply section 800 of the sensor drive section 300.

The sensor drive section 300 includes a sensor control section 600, the electric circuit section 700, and the air supply section 800. The sensor control section 600 and the electric circuit section 700 are electrically connected to each other, and the sensor control section 600 and the air supply section 800 are electrically connected to each other.

The sensor control section 600 includes a microcomputer, and controls the electric circuit section 700 and the air supply section 800. Also, the sensor control section 600 detects (measures) the amount of particulates contained in the exhaust gas from a signal supplied from the electric circuit section 700, and outputs to the vehicle control section 420 a signal representing the amount of particulates contained in the exhaust gas.

The electric circuit section 700 supplies electric power for driving the particulate sensor 100 through the first wiring line 221 and the second wiring line 222. A signal which correlates with the amount of particulates contained in the exhaust gas is input from the particulate sensor 100 to the electric circuit section 700 through the signal line 223. Using this signal input through the signal line 223, the electric circuit section 700 outputs to the sensor control section 600 a signal corresponding to the amount of particulates contained in the exhaust gas. These signals will be described in detail below.

The air supply section 800 includes a pump (not shown), and supplies high-pressure air to the particulate sensor 100 through the air supply tube 224 based on an instruction from the sensor control section 600. The high-pressure air supplied from the air supply section 800 is used to drive the particulate sensor 100. Notably, the type of gas supplied by the air supply section 800 may be other than air.

[1-2. Particulate Sensor]

Figure 2:
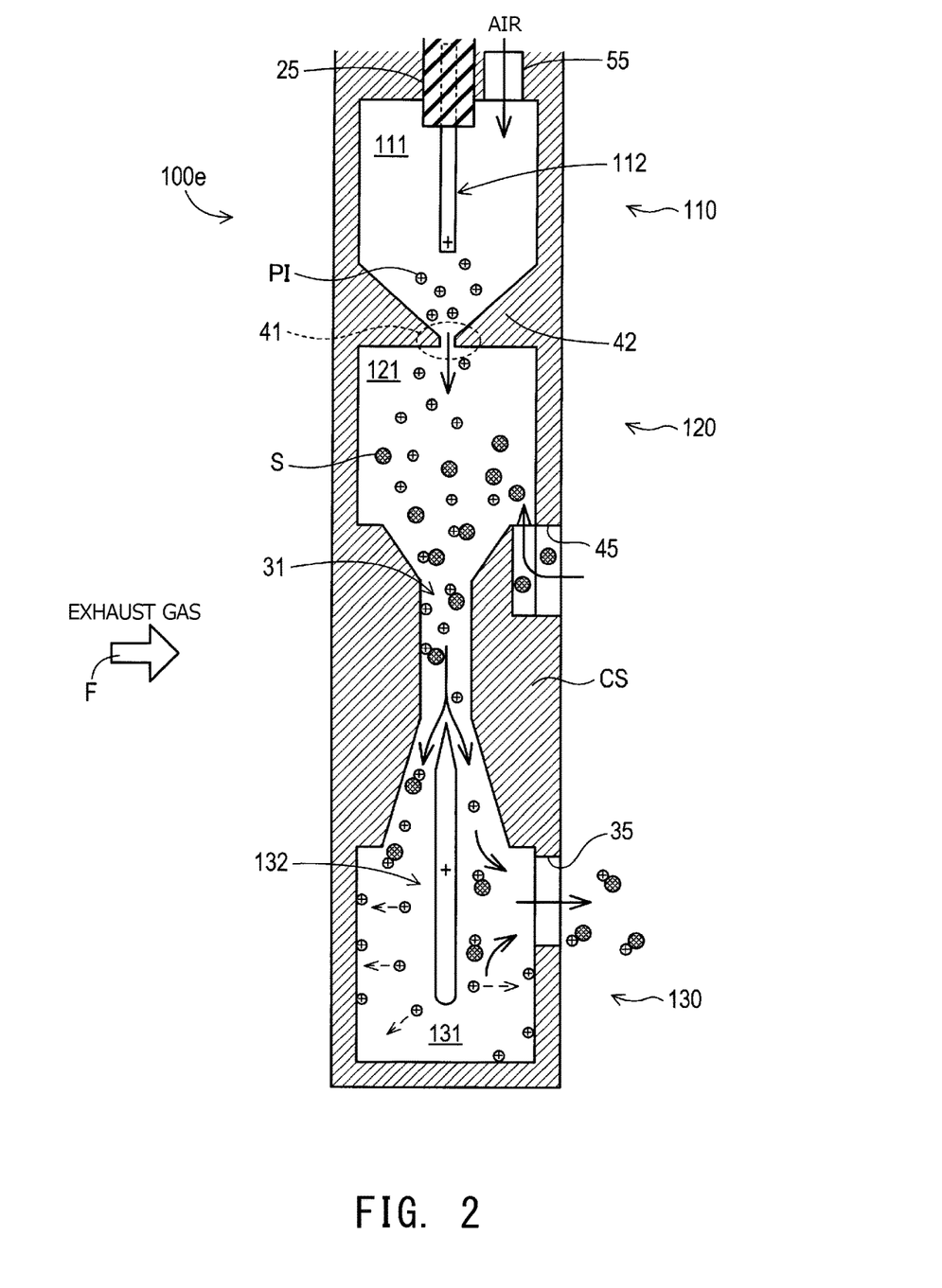
FIG. 2 is an explanatory view schematically showing a general structure of a distal end portion of a particulate sensor.

FIG. 2 is an explanatory view schematically showing a general structure of the distal end portion 100e of the particulate sensor 100.

The distal end portion 100e of the particulate sensor 100 includes an ion generation section 110, an exhaust gas electrification section 120, and an ion trapping section 130. The casing CS has a structure in which the three mechanism sections; i.e., the ion generation section 110, the exhaust gas electrification section 120, and the ion trapping section 130, are arranged in this order from the proximal end side (the upper side in FIG. 2) of the distal end portion 100e toward the distal end side (the lower side in FIG. 2) thereof (along the axial direction of the particulate sensor 100). The casing CS is formed of an electrically conductive material, and is connected to a secondary-side ground SGL (FIG. 3) through the signal line 223 (FIG. 1B).

The ion generation section 110 is a mechanism section for generating ions (positive ions in the present embodiment) which are supplied to the exhaust gas electrification section 120. The ion generation section 110 includes an ion generation chamber 111 and a first electrode 112. The ion generation chamber 111 is a small space formed inside the casing CS. An air supply hole 55 and a nozzle 41 are provided on the inner circumferential surface of the ion generation chamber 111. The first electrode 112 is attached such that it projects into the ion generation chamber 111. The air supply hole 55 communicates with the air supply tube 224 (FIG. 1B), and high-pressure air supplied from the air supply section 800 (FIG. 1B) is supplied to the ion generation chamber 111 through the air supply hole 55. The nozzle 41 is a very small hole (orifice) provided near the center of a partition wall 42 which separates the ion generation section 110 and the exhaust gas electrification section 120. The nozzle 41 supplies the ions generated in the ion generation chamber 111 to an electrification chamber 121 of the exhaust gas electrification section 120. The first electrode 112 has a rod-like outer shape, and its base end portion is fixed to the casing CS via a ceramic pipe 25 in a state in which a distal end portion of the first electrode 112 is located near the partition wall 42. The first electrode 112 is connected to the electric circuit section 700 (FIG. 1B) through the first wiring line 221 (FIG. 1B).

The ion generation section 110 is configured such that, by electric power supplied from the electric circuit section 700, a voltage (e.g., 2 to 3 kV) is applied between the first electrode 112 (positive pole) and the partition wall 42 (negative pole). As a result of applying this voltage, the ion generation section 110 produces a corona discharge between a distal end portion of the first electrode 112 and the partition wall 42 to thereby generate positive ions PI. The positive ions PI generated in the ion generation section 110 are jetted into the electrification chamber 121 of the exhaust gas electrification section 120 through the nozzle 41 together with the high-pressure air supplied from the air supply section 800 (FIG. 1B). The jetting speed of air jetted from the nozzle 41 may be set to a speed near the speed of sound.

The exhaust gas electrification section 120 is a section for electrifying the particulates contained in the exhaust gas by positive ions PI, and includes the electrification chamber 121. The electrification chamber 121 is a small space located adjacent to the ion generation chamber 111, and communicates with the ion generation chamber 111 through the nozzle 41. Also, the electrification chamber 121 communicates with the outside of the casing CS through the inflow hole 45, and communicates with a trapping chamber 131 of the ion trapping section 130 through a gas flow passage 31. The electrification chamber 121 is configured such that, when air containing the positive ions PI is jetted from the nozzle 41, a negative pressure is created in the electrification chamber 121, and the exhaust gas located outside the casing CS flows into the electrification chamber 121 through the inflow hole 45. Therefore, the air jetted from the nozzle 41 and containing the positive ions PI and the exhaust gas flowing inward through the inflow hole 45 are mixed together within the electrification chamber 121. At that time, at least a portion of the soot S (particulates) contained in the exhaust gas and which has flowed inward through the inflow hole 45 is electrified by the positive ions PI supplied from the nozzle 41. The air containing the electrified soot S and the positive ions PI not used for the electrification is supplied to the trapping chamber 131 of the ion trapping section 130 through the gas flow passage 31.

The ion trapping section 130 is a section for trapping ions not used for the electrification of the soot S (particulates), and includes the trapping chamber 131 and a second electrode 132. The trapping chamber 131 is a small space located adjacent to the electrification chamber 121, and communicates with the electrification chamber 121 through the gas flow passage 31. Also, the trapping chamber 131 communicates with the outside of the casing CS through the discharge hole 35. The second electrode 132 has a generally rod-like outer shape and is fixed to the casing CS such that its longitudinal direction coincides with the flow direction of air flowing through the gas flow passage 31 (the extending direction of the casing CS). The second electrode 132 is connected to the electric circuit section 700 (FIG. 1B) through the second wiring line 222 (FIG. 1B). The second electrode 132 is electrically insulated from the casing CS.

A voltage of about 100 V is applied to the second electrode 132, whereby it functions as an auxiliary electrode for assisting the trapping of positive ions not used for the electrification of the soot S. Specifically, by the electric power supplied from the electric circuit section 700, a voltage is applied to the ion trapping section 130 such that the second electrode 132 serves as a positive pole, and the casing CS constituting the electrification chamber 121 and the trapping chamber 131 serves as a negative pole. As a result, the positive ions PI not used for the electrification of soot S are repulsed by the second electrode 132, whereby their advancing directions deviate to directions away from the second electrode 132. The deviated positive ions PI are trapped by the inner circumferential walls of the trapping chamber 131 and the gas flow passage 31 which function as a negative pole. Meanwhile, the soot S to which positive ions PI have adhered are also subject to the repulsive force from the second electrode 132 as in the case of the positive ions PI themselves. However, since the soot S are larger in mass than the positive ions PI, the influence of the repulsive force on the advancing directions is smaller as compared with the case of the positive ions PI themselves. Therefore, the electrified soot S is discharged to the outside of the casing CS through the discharge hole 35 as a result of the flow of the exhaust gas.

The particulate sensor 100 outputs a signal showing a change in current which corresponds to the amount of positive ions PI trapped in the ion trapping section 130. The sensor control section 600 (FIG. 1B) detects the amount of soot S contained in the exhaust gas based on the signal output from the particulate sensor 100.

[1-3. Electric Circuit Section]

Figure 3:
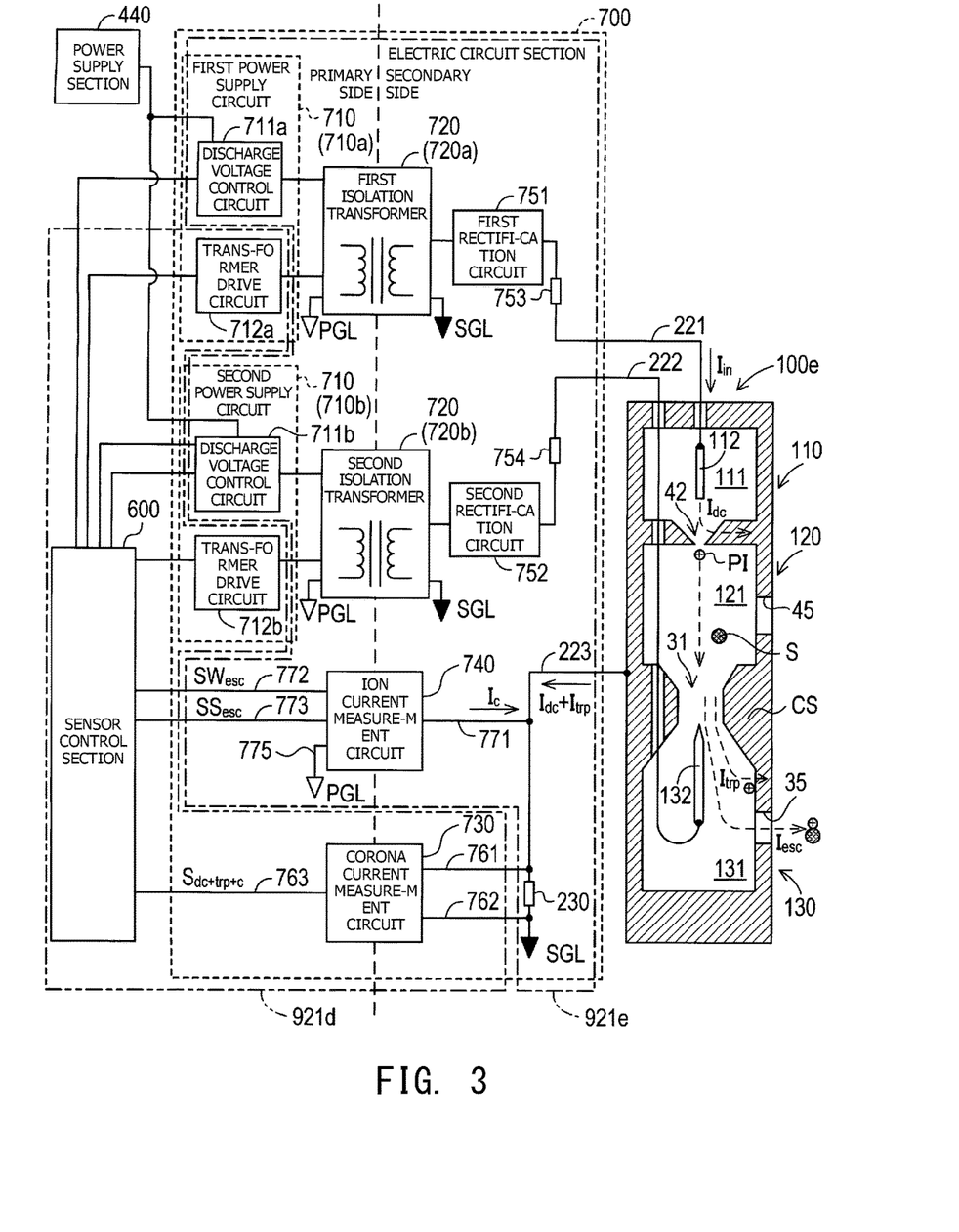
FIG. 3 is an explanatory view exemplifying a general configuration of an electric circuit section.

FIG. 3 is an explanatory view exemplifying a general configuration of the electric circuit section 700.

The electric circuit section 700 includes a power supply circuit 710, an isolation transformer 720, a corona current measurement circuit 730, an ion current measurement circuit 740, a first rectification circuit 751, and a second rectification circuit 752.

The power supply circuit 710 includes a first power supply circuit 710a and a second power supply circuit 710b. The isolation transformer 720 includes a first isolation transformer 720a and a second isolation transformer 720b.

The first power supply circuit 710a steps up the voltage of electric power supplied from the power supply section 440, supplies the stepped up voltage to the first isolation transformer 720a, and drives the first isolation transformer 720a. The first power supply circuit 710a includes a first discharge voltage control circuit 711a and a first transformer drive circuit 712a. The first discharge voltage control circuit 711a is configured such that it can arbitrarily change the voltage value of the electric power supplied to the first isolation transformer 720a under control of the sensor control section 600. In the present embodiment, the sensor control section 600 controls the voltage value of the electric power supplied to the first isolation transformer 720a such that an input current $I_{in}$ supplied to the first electrode 112 of the particulate sensor 100 through the first wiring line 221 becomes equal to a target current $I_{ta}$ (e.g., 5 μA) set in advance. As a result, the amount of positive ions PI generated by the corona discharge in the ion generation section 110 can be made constant.

The first transformer drive circuit 712a includes a switch which can switch the flow direction of current flowing through the primary coil (primary winding) of the first isolation transformer 720a. The first transformer drive circuit 712a drives the first isolation transformer 720a by the switching operation of the switch. In the present embodiment, the circuit type of the first isolation transformer 720a is a push-pull type. However, the circuit type of the first isolation transformer 720a is not limited thereto and may be, for example, a half-bridge type or a full-bridge type circuit.

The first isolation transformer 720a performs voltage conversion for the electric power supplied from the first power supply circuit 710a, and supplies the voltage-converted electric power to the first rectification circuit 751 on the secondary side. The first isolation transformer 720a of the present embodiment is configured such that the primary coil (primary winding) and the secondary coil (secondary winding) are not in physical contact with each other but are magnetically coupled with each other. A circuit on the primary side of the first isolation transformer 720a includes the sensor control section 600 and the power supply section 440 as well as the first power supply circuit 710a. A circuit on the secondary side of the first isolation transformer 720a includes the particulate sensor 100 and the first rectification circuit 751.

The second power supply circuit 710b steps up the voltage of electric power supplied from the power supply section 440, supplies the stepped up voltage to the second isolation transformer 720b, and drives the second isolation transformer 720b. The second power supply circuit 710b includes a second discharge voltage control circuit 711b and a second transformer drive circuit 712b. The second discharge voltage control circuit 711b is configured such that it can arbitrarily change the voltage value of the electric power supplied to the second isolation transformer 720b under control of the sensor control section 600. In the present embodiment, the sensor control section 600 controls the voltage value of the electric power supplied to the second isolation transformer 720b such that the voltage supplied to the second electrode 132 of the particulate sensor 100 through the second wiring line 222 becomes equal to a target voltage (e.g., 100 V) set in advance.

The second transformer drive circuit 712b includes a switch which can switch the flow direction of current flowing through the primary coil of the second isolation transformer 720b. The second transformer drive circuit 712b drives the second isolation transformer 720b by the switching operation of the switch. In the present embodiment, the circuit type of the second isolation transformer 720b is a push-pull type. However, the circuit type of the second isolation transformer 720b is not limited thereto and may be, for example, a half-bridge type or a full-bridge type circuit.

The second isolation transformer 720b performs voltage conversion for the electric power supplied from the second power supply circuit 710b, and supplies the voltage-converted electric power to the second rectification circuit 752 on the secondary side. The second isolation transformer 720b of the present embodiment is configured such that the primary coil and the secondary coil are not in physical contact with each other but are magnetically coupled with each other. A circuit on the primary side of the second isolation transformer 720b includes the sensor control section 600 and the power supply section 440 as well as the second power supply circuit 710b. A circuit on the secondary side of the second isolation transformer 720b includes the particulate sensor 100 and the second rectification circuit 752.

The corona current measurement circuit 730 and the ion current measurement circuit 740 are circuits provided between the circuit on the primary side of the isolation transformer 720 (the first isolation transformer 720a and the second isolation transformer 720b) and the circuit on the secondary side of the isolation transformer 720 (the first isolation transformer 720a and the second isolation transformer 720b), and are electrically connected to the primary-side and secondary-side circuits, respectively.

The corona current measurement circuit 730 is configured such that a circuit portion electrically connected to the circuit on the primary side of the isolation transformer 720 (the first isolation transformer 720a and the second isolation transformer 720b) is physically insulated from a circuit portion electrically connected to the circuit on the secondary side of the isolation transformer 720 (the first isolation transformer 720a and the second isolation transformer 720b). Here, a ground (ground wiring) which has the reference potential of the primary-side circuit is also referred to as a "primary-side ground PGL," and a ground which has the reference potential of the secondary-side circuit is also referred to as a "secondary-side ground SGL."

The corona current measurement circuit 730 is configured as a so-called optical-coupling-type isolation amplifier in which its input side portion (a portion connected to the circuit on the secondary side) and its output side portion (a portion connected to the circuit on the primary side) are electrically isolated from each other. Namely, the input side portion of the corona current measurement circuit 730 amplifies an analog voltage signal representing the current value of the current flowing through the signal line 223 (FIG. 3), converts the analog voltage signal to a digital voltage signal, and then converts the digital voltage signal to an optical signal. This input portion includes a light emitting section having an LED, and the optical signal which changes with the current value of the current flowing through the signal line 223 is output from the light emitting section to the output side portion of the corona current measurement circuit 730. The output side portion of the corona current measurement circuit 730 includes a light receiving section having a photo diode, and this light receiving section receives the optical signal output from the light emitting section of the input side portion of the corona current measurement circuit 730 and converts the optical signal to a current signal. The corona current measurement circuit 730 is configured such that the light emitting section of the input side portion and the light receiving section of the output side portion are electrically and physically isolated from each other, and signal transmission therebetween is performed through use of light. The output side portion of the corona current measurement circuit 730 converts the current signal output from the light receiving section to a digital voltage signal through use of a current-voltage conversion circuit, converts this digital voltage signal to an analog voltage signal, and outputs the analog voltage signal to the sensor control section 600. As a result of having the above-described configuration, the corona current measurement circuit 730 can output the signal input from the signal line 223 on the secondary side to the sensor control section 600 on the primary side while maintaining the isolation between the primary side and the secondary side.

Ends of the primary coils of the isolation transformer 720 (the first isolation transformer 720a and the second isolation transformer 720b) are connected to the primary-side ground PGL, and ends of the secondary coils thereof are connected to the secondary-side ground SGL. One end of the signal line 223 is connected to the casing CS, and the other end of the signal line 223 is connected to the secondary-side ground SGL.

The first rectification circuit 751 is connected to the first electrode 112 through a short protection resistor 753, and supplies the converted electric power to the first electrode 112 through the first wiring line 221. Namely, the voltage supplied from the first rectification circuit 751 becomes mostly a discharge voltage at the first electrode 112, and the current supplied from the first rectification circuit 751 becomes an input current Iin input to the first electrode 112. The second rectification circuit 752 is connected to the second electrode 132 through a short protection resistor 754, and applies the converted voltage to the second electrode 132 through the second wiring line 222.

The ion current measurement circuit 740 detects the current value of a current ($I_{esc}$) corresponding to the positive ions PI which have flowed out without having been trapped by the ion trapping section 130 and supplies to the secondary-side circuit a current (compensation current $I_c$) corresponding to the positive ions PI which have flowed out. The ion current measurement circuit 740 is connected to the signal line 223 on the secondary side (specifically, a portion of the signal line 223 located between the casing CS and the shunt resistor 230) through a wiring line 771, and is connected to the sensor control section 600 on the primary side through wiring lines 772 and 773. Also, the ion current measurement circuit 740 is connected to the primary-side ground PGL through the wiring line 775. Through the wiring line 772, the ion current measurement circuit 740 outputs to the sensor control section 600 a signal $SW_{esc}$ indicating the current value of the current ($I_{esc}$) corresponding to the amount of positive ions PI which have flowed out without having been trapped by the ion trapping section 130. The ion current measurement circuit 740 also outputs a signal $SS_{esc}$ to the sensor control section 600 through the wiring line 773, the signal $SS_{esc}$ being obtained by amplifying the signal $SW_{esc}$ and serving as a high sensitivity signal.

The corona current measurement circuit 730 is connected to the signal line 223 through wiring lines 761 and 762, and is connected to the sensor control section 600 through a wiring line 763. The wiring lines 761 and 762 are connected to the signal line 223 such that the shunt resistor 230 provided in the signal line 223 is located between the wiring lines 761 and 762. The corona current measurement circuit 730 outputs to the sensor control section 600 a signal $S_{dc+trp+c}$ representing the current value of a secondary-side current ($I_{dc}+I_{trp}+I_c$) flowing from the casing CS toward the secondary-side ground SGL through the signal line 223. Here, a "signal representing the current value" is not limited to a signal which directly represents the current value, and may be a signal which indirectly represents the current value. For example, the "signal representing the current value" may be a signal on the basis of which the current value can be specified by applying a computation expression or a map to information obtained from the signal. Notably, since the compensation current $I_c$ supplied (supplemented) from the ion current measurement circuit 740 corresponds to the current corresponding to the positive ions PI which have flowed out of the casing CS, the current value of the secondary-side current which includes the compensation current $I_c$ and which flows from the casing CS to the secondary-side ground SGL; i.e., the current value of the secondary-side current ($I_{dc}+I_{trp}+I_c$) flowing through the shunt resistor 230, becomes equal to the current value of the input current $I_{in}$.

Using the signal $S_{dc+trp+c}$ input from the corona current measurement circuit 730, the sensor control section 600 controls the first discharge voltage control circuit 711a such that the current value of the input current $I_{in}$ becomes equal to the target current $I_{ta}$. Namely, the corona current measurement circuit 730 and the sensor control section 600 constitute a constant current circuit for maintaining the current value of the corona current (=the input current $I_{in}$) at a constant level. Since the current value of the corona current correlates with the amount of positive ions PI generated at the ion generation section 110, the amount of positive ions PI generated at the ion generation section 110 is maintained constant by this constant current circuit.

A method will be described by which the ion current measurement circuit 740 detects the current value of the current corresponding to the positive ions PI which have flowed out without having been trapped by the ion trapping section 130.

Here, the current supplied from the first wiring line 221 to the first electrode 112 is referred to as the "input current $I_{in}$"; the current flowing from the first electrode 112 to the casing CS through the partition wall 42 due to corona discharge is referred to as the "discharge current $I_{dc}$"; the current corresponding to the charge of the positive ions PI which are some of the positive ions PI generated due to corona discharge, are used for electrification of the soot S, and leak to the outside of the casing CS is referred to as the "signal current $I_{esc}$"; and the current corresponding to the charge of the positive ions PI trapped by the casing CS is referred to as the "trapped current $I_{trp}$." These four currents satisfy the relation of expression (1) shown below.

$$I_{in}=I_{dc}+I_{trp}+I_{esc} \quad (1)$$

Here, the signal current $I_{esc}$ is a signal which is output from the ion current measurement circuit 740 and which represents a current value corresponding to the current (the compensation current $I_c$) corresponding to the positive ions PI which have flowed out. Therefore, by detecting this compensation current $I_c$, the ion current measurement circuit 740 can detect the current value of the current ($I_{esc}$) corresponding to the positive ions PI which have flowed out without having been trapped by the ion trapping section 130. Notably, the compensation current $I_c$ is also a signal representing the potential difference between the primary-side ground PGL and the secondary-side ground SGL.

[1-4. Circuit Housing]

Figure 4:
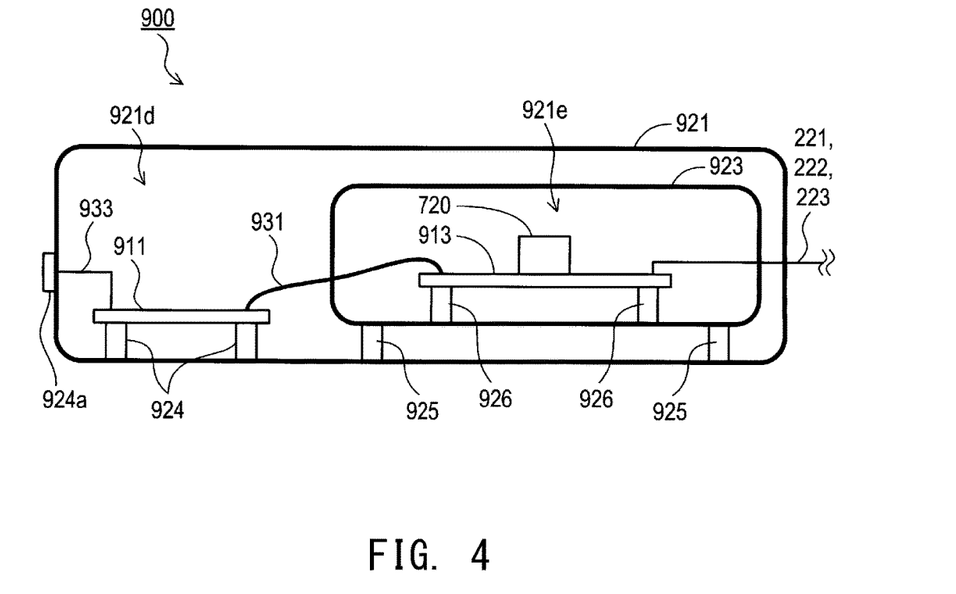
FIG. 4 is a view schematically showing the electromagnetic shield structure of a circuit housing.

Next, a circuit housing 900 which houses the electric circuit section 700 and the sensor control section 600 will be described.

FIG. 4 is a view schematically showing the electromagnetic shield structure of the circuit housing 900.

The circuit housing 900 includes an outer case 921 and an inner case 923. Each of the outer case 921 and the inner case 923 is a container formed of a metallic material (e.g., aluminum, copper, iron, or the like) which blocks electromagnetic noise. The outer case 921 is connected to the primary-side ground PGL. The inner case 923 is connected to the secondary-side ground SGL.

The outer case 921 accommodates a control board 911 and the inner case 923.

The control board 911 is a circuit board which includes the sensor control section 600, the first transformer drive circuit 712a, the second transformer drive circuit 712b, and the corona current measurement circuit 730. The control board 911 is electrically insulated from the outer case 921 by a first insulating member 924.

The first insulating member 924 is formed of a resin material such as PPS (polyphenylene sulfide) or PBT (polybutylene terephthalate). The first insulating member 924 has a power supply connection portion 924a. The power supply connection portion 924a is a connector for connecting to the power supply section 440. The power supply connection portion 924a include metallic terminals (not shown) which are electrically connected to the control board 911 through a cable 933.

The inner case 923 is electrically insulated from the outer case 921 by a second insulating member 925. The second insulating member 925 is formed of a resin material such as PPS or PBT.

The inner case 923 accommodates a high voltage generation board 913 and the isolation transformer 720.

The high voltage generation board 913 is a circuit board which includes the first discharge voltage control circuit 711a, the second discharge voltage control circuit 711b, the ion current measurement circuit 740, the first rectification circuit 751, the second rectification circuit 752, the short protection resistor 753, the short protection resistor 754, and the shunt resistor 230. The high voltage generation board 913 is connected to the particulate sensor 100 through the first wiring line 221, the second wiring line 222, and the signal line 223. The high voltage generation board 913 is electrically insulated from the inner case 923 by a third insulating member 926. The third insulating member 926 is formed of a resin material such as PPS or PBT.

The circuit housing 900 accommodates a double shield wire 931 which connects the control board 911 and the high voltage generation board 913. The double shield wire 931 includes signal lines for conveying various signals, current, etc., between the control board 911 and the high voltage generation board 913, and a shield layer which covers the signal lines and shields them from electromagnetic noise. The shield layer is composed of an inner shield layer which covers the signal lines, and an outer shield layer which covers the inner shield layer. One of the inner shield layer and the outer shield layer is connected to the primary-side ground PGL, and the other of the inner shield layer and the outer shield layer is connected to the secondary-side ground SGL.

Figure 5:
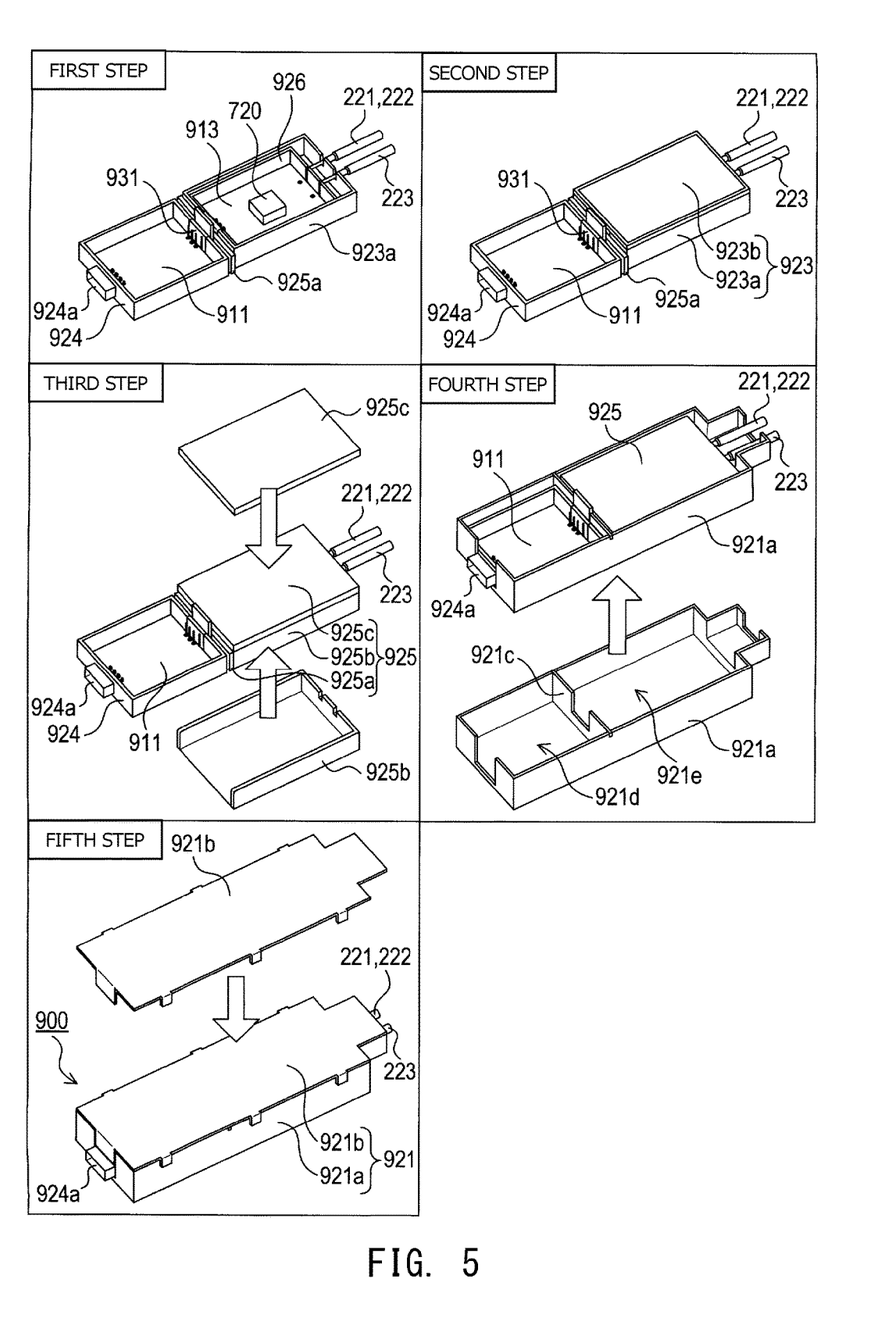
FIG. 5 shows the steps of a process of manufacturing the circuit housing.

Next, a process of manufacturing the circuit housing 900 will be described.

FIG. 5 is a set of explanatory views showing the steps of the process of manufacturing the circuit housing 900.

First, in a first step, work is performed for integrally fixing an inner body member 923a which is a portion of the inner case 923 and the first insulating member 924.

At that time, an insulating gap member 925a which is a portion of the second insulating member 925 is disposed between the inner body member 923a and the first insulating member 924. The third insulating member 926 is disposed inside the inner body member 923a. The high voltage generation board 913 and the isolation transformer 720 are disposed inside the third insulating member 926. The control board 911 is disposed inside the first insulating member 924. The control board 911 and the high voltage generation board 913 are connected to each other through the double shield wire 931.

In a second step subsequent thereto, work is performed for disposing an inner cover member 923b which is a portion of the inner case 923 to cover the opening of the inner body member 923a. As a result, the inner case 923 having the inner body member 923a and the inner cover member 923b is completed. The inner case 923 accommodates the high voltage generation board 913, the isolation transformer 720, and the third insulating member 926.

In a third step subsequent thereto, work is performed for disposing an insulating housing member 925b which is a portion of the second insulating member 925 so as to be located outside the inner case 923, and then disposing an insulating cover member 925c which is a portion of the second insulating member 925 to cover the opening of the insulating housing member 925b. As a result, the second insulating member 925 having the insulating gap member 925a, the insulating housing member 925b, and the insulating cover member 925c is completed. The second insulating member 925 accommodates the inner case 923.

In a fourth step subsequent thereto, work is performed for disposing the first insulating member 924 and the second insulating member 925 inside an outer body member 921a which is a portion of the outer case 921. The outer body member 921a has a partition wall 921c provided therein. The partition wall 921c divides the inner space of the outer body member 921a into a first space 921d and a second space 921e. The first space 921d is a space for disposing the first insulating member 924, and the second space 921e is a space for disposing the second insulating member 925.

In a fifth step subsequent thereto, work is performed for disposing an outer cover member 921b which is a portion of the outer case 921 to cover the opening of the outer body member 921a. As a result, the outer case 921 having the outer body member 921a and the outer cover member 921b is completed. The outer case 921 accommodates the first insulating member 924 and the second insulating member 925.

As a result, the circuit housing 900 is completed.

In the circuit housing 900 having the above-described configuration, the inner case 923 covers the high voltage generation board 913 and the isolation transformer 720, and the outer case 921 covers the control board 911 (the first transformer drive circuit 712a, the second transformer drive circuit 712b, the sensor control section 600, and the corona current measurement circuit 730) and the inner case 923.

As a result, the control board 911 (the first transformer drive circuit 712a, the second transformer drive circuit 712b, the sensor control section 600, and the corona current measurement circuit 730) is disposed in the first space 921d which is a space located inside the outer case 921 and located outside the inner case 923. The high voltage generation board 913 and the isolation transformer 720 are disposed in the second space 921e which is a space located inside the inner case 923.

Namely, the circuit housing 900 is configured such that "the control board 911 (the first transformer drive circuit 712a, the second transformer drive circuit 712b, the sensor control section 600, and the corona current measurement circuit 730)" and "the high voltage generation board 913 and the isolation transformer 720" are respectively disposed in two different spaces (the first space 921d and the second space 921e) separated from each other by the inner case 923.

Notably, FIG. 3 also show regions corresponding to the first space 921d and the second space 921e.

[1-5. Effects]

As described above, the particulate detection system 10 of the present embodiment includes the particulate sensor 100, the high voltage generation board 913, the isolation transformer 720, the control board 911 (the first transformer drive circuit 712a, the second transformer drive circuit 712b, the sensor control section 600, and the corona current measurement circuit 730), and the circuit housing 900.

The high voltage generation board 913 and the isolation transformer 720 supplies to the particulate sensor 100 a high voltage generated from the secondary winding as a result of switching the primary current supply to the primary winding. Specifically, the high voltage generated from the secondary winding of the first isolation transformer 720a as a result of switching the primary current supply to the primary winding thereof is supplied to the first electrode 112 of the particulate sensor 100. Similarly, the high voltage generated from the secondary winding of the second isolation transformer 720b as a result of switching the primary current supply to the primary winding thereof is supplied to the second electrode 132 of the particulate sensor 100.

The first transformer drive circuit 712a controls the primary current flowing through the primary winding of the first isolation transformer 720a. The second transformer drive circuit 712b controls the primary current flowing through the primary winding of the second isolation transformer 720b.

The sensor control section 600 processes the sensor signal generated by the particulate sensor 100. Specifically, the sensor control section 600 detects (measures) the amount of particulates contained in the exhaust gas from the signal input from the electric circuit section 700, and outputs to the vehicle control section 420 a signal representing the amount of particulates contained in the exhaust gas.

The circuit housing 900 includes the outer case 921 and the inner case 923. The inner case 923 covers the high voltage generation board 913 and the isolation transformer 720, and is formed of a metallic material which blocks electromagnetic noise. The outer case 921 covers the control board 911 (the first transformer drive circuit 712a, the second transformer drive circuit 712b, the sensor control section 600, and the corona current measurement circuit 730) and the inner case 923, and is formed of a metallic material which blocks electromagnetic noise.

As a result, the control board 911 (the first transformer drive circuit 712a, the second transformer drive circuit 712b, the sensor control section 600, and the corona current measurement circuit 730) is disposed in the first space 921d which is a space located inside the outer case 921 and located outside the inner case 923. The high voltage generation board 913 and the isolation transformer 720 are disposed in the second space 921e which is a space inside the inner case 923.

Namely, in the particulate detection system 10, "the control board 911 (the first transformer drive circuit 712a, the second transformer drive circuit 712b, the sensor control section 600, and the corona current measurement circuit 730)" and "the high voltage generation board 913 and the isolation transformer 720" are respectively disposed in two different spaces (the first space 921d and the second space 921e) separated from each other by the inner case 923.

In the case where the particulate detection system 10 has such a structure, even when electromagnetic noise is generated in "the high voltage generation board 913 and the isolation transformer 720" at the time of switching the primary current supply, the electromagnetic noise is blocked by the inner case 923. Therefore, it is possible to reduce the influence of electromagnetic noise generated in the primary winding on "the control board 911 (the first transformer drive circuit 712a, the second transformer drive circuit 712b, the sensor control section 600, and the corona current measurement circuit 730)."

Also, since the outer case 921 is provided, external electromagnetic noise is prevented from reaching the control board 911. Therefore, it is possible to reduce the influence of external noise on the control board 911.

As a result, the present particulate detection system 10 can reduce the influence of the electromagnetic noise generated in the primary winding on the control board 911 (the first transformer drive circuit 712a, the second transformer drive circuit 712b, the sensor control section 600, and the corona current measurement circuit 730). Thus, the present particulate detection system 10 can suppress a decrease in particulate detection accuracy due to the influence of electromagnetic noise. Further, the present particulate detection system 10 can reduce the influence of external electromagnetic noise on the control board 911 (the first transformer drive circuit 712a, the second transformer drive circuit 712b, the sensor control section 600, and the corona current measurement circuit 730).

[1-6. Term Correspondence]

Here, corresponding terms of the invention used to identify various structural features in the above embodiment are as follows.

The particulate detection system 10 corresponds to the particulate detection system of the invention; the particulate sensor 100 corresponds to the particulate sensor of the invention; the high voltage generation board 913 and the isolation transformer 720 correspond to the high voltage generation section of the invention; the isolation transformer 720 corresponds to the transformer of the invention; and the first transformer drive circuit 712a and the second transformer drive circuit 712b correspond to the primary current control section of the invention. The sensor control section 600 corresponds to the sensor signal processing section of the invention; the inner case 923 corresponds to the inner shield of the invention; and the outer case 921 corresponds to the outer shield of the invention.

2. Other Embodiments

An embodiment of the present invention has been described; however, the present invention is not limited thereto and can be implemented in various forms without departing from the gist of the invention.

Figure 6:
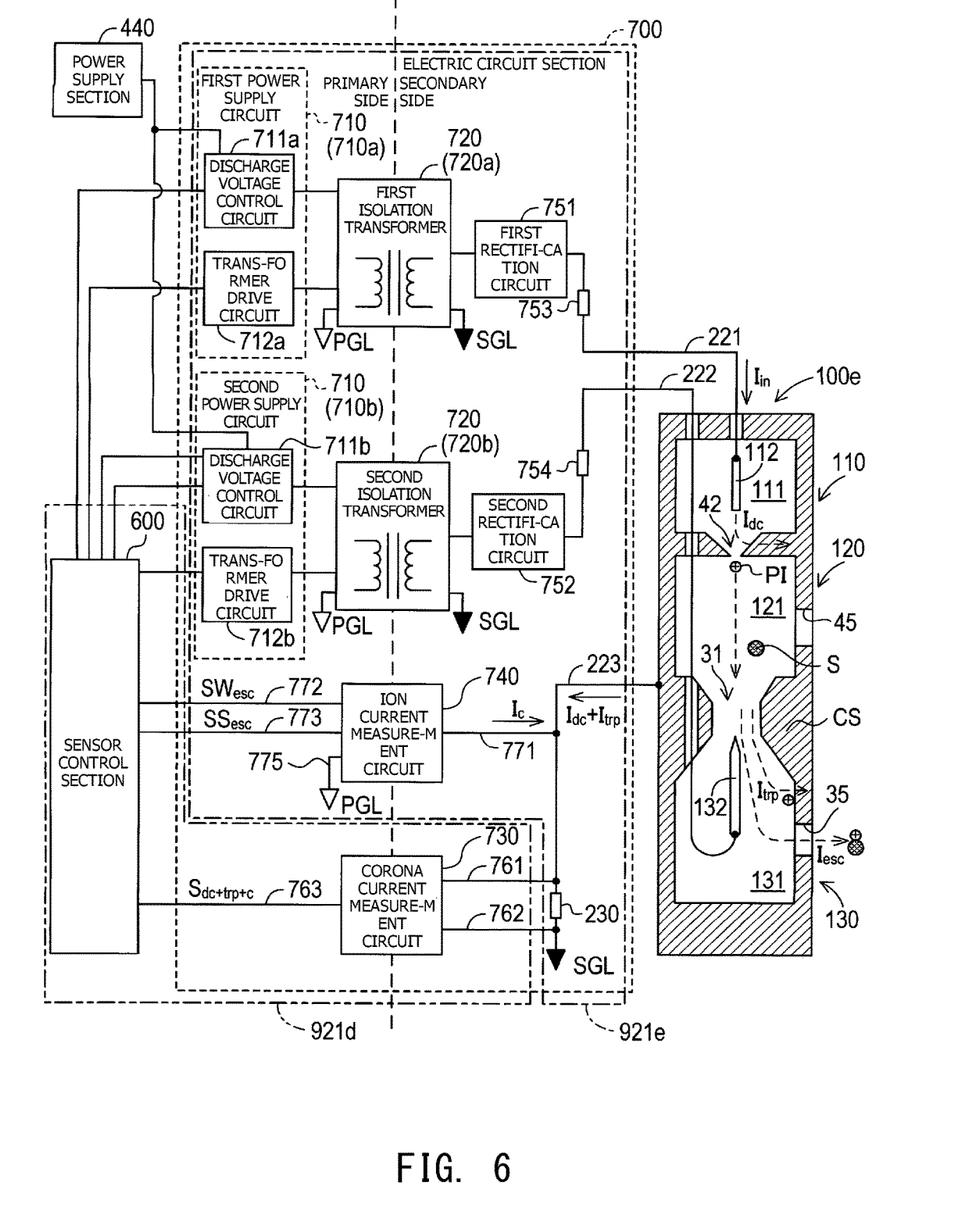
FIG. 6 is an explanatory view showing regions corresponding to first and second spaces in a configuration in which a first transformer drive circuit and a second transformer drive circuit are disposed on a high voltage generation board (second space).

For example, in the above-described embodiment, the particulate detection system 10 is configured such that the first transformer drive circuit 712a and the second transformer drive circuit 712b are disposed on the control board 911 (in other words, in the first space 921d). However, the present invention is not limited to such a configuration. For example, the particulate detection system 10 may be configured such that the first transformer drive circuit 712a and the second transformer drive circuit 712b are disposed on the high voltage generation board 913 (in the second space 921e). FIG. 6 is an explanatory diagram showing regions corresponding to the first space 921d and the second space 921e in such a configuration.

Such a configuration is effective for the case where a transformer drive circuit which generates electromagnetic noise influencing the sensor control section 600 and the corona current measurement circuit 730 is used as the first transformer drive circuit 712a and the second transformer drive circuit 712b. Namely, even when electromagnetic noise is generated in the first transformer drive circuit 712a and the second transformer drive circuit 712b, the inner case 923 can block the electromagnetic noise, to thereby suppress the influence of electromagnetic noise on the sensor control section 600 and the corona current measurement circuit 730. Accordingly, a particulate detection system having such a configuration can suppress a decrease in particulate detection accuracy due to the influence of the electromagnetic noise generated in the first transformer drive circuit 712a and the second transformer drive circuit 712b.

Also, in the above-described embodiment, the particulate sensor 100 has the second electrode 132. However, the particulate sensor may be configured without use of the second electrode 132. Even when the second electrode 132 is omitted, the amount of particulates can be measured based on the amount of electrified particulates, and the structure of the particulate sensor can be simplified to a degree corresponding to the omission of the second electrode 132. In such a case, the second power supply circuit 710b, the second isolation transformer 720b, the second rectification circuit 752, the short protection resistor 754, and the second wiring line 222 may be omitted from the electric circuit section 700.

Also, the structure of the particulate sensor which constitutes the particulate detection system is not limited to a structure in which the ion generation section is disposed in line outside the exhaust gas electrification section. For example, a structure can be employed in which the ion generation section is disposed inside the exhaust gas electrification section. Further, in the case where the particulate sensor constituting the particulate detection system is configured such that the ion generation section is disposed inside the exhaust gas electrification section, the air supply section may be omitted from the sensor drive section, and the particulate sensor may have a structure in which high-pressure air is not supplied to the electrification chamber. For example, such a particulate sensor may have a sensor structure as disclosed in US 2015/0192545 published Jul. 9, 2015 by the present applicants, the disclosure of which is incorporated herein by reference in its entirety. Also, the corona current measurement circuit is not limited to an optical-coupling-type isolation amplifier and may be, for example, a magnetic-coupling-type or capacitive-coupling-type isolation amplifier.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2016-106566 filed May 27, 2016, incorporated herein by reference in its entirety.

What is claimed is:

1. A particulate detection system comprising:
    a particulate sensor which generates a sensor signal corresponding to a result of particulate detection;
    a high voltage generation section which includes a transformer having a primary winding and a secondary winding, and which supplies to the particulate sensor a high voltage generated from the secondary winding as a result of switching a primary current supply to the primary winding;
    a primary current control section which controls the primary current flowing through the primary winding; and
    a sensor signal processing section which processes the sensor signal generated by the particulate sensor,
    the particulate detection system further comprising:
    an inner shield which covers the high voltage generation section and which is formed of a material which blocks electromagnetic noise; and
    an outer shield which covers the sensor signal processing section and the inner shield, and which is formed of a material which blocks electromagnetic noise,
    wherein the entire high voltage generation section is provided inside the inner shield and the sensor signal processing section is disposed inside the outer shield and outside the inner shield.

2. The particulate detection system as claimed in claim 1, wherein the primary current control section is disposed inside the inner shield.

* * * * *